United States Patent [19]

Buck et al.

[11] Patent Number: 4,723,989
[45] Date of Patent: Feb. 9, 1988

[54] HERBICIDAL IMIDAZOLINONES

[75] Inventors: Wolfgang Buck, Ingelheim; Manfred Garrecht, Wackernheim; Gerhart Schneider, Mühltal; Christo Drandarevski, Ingelheim, all of Fed. Rep. of Germany

[73] Assignee: Celarmerck GmbH & Co. KG, Ingelheim am Rhein, Fed. Rep. of Germany

[21] Appl. No.: 943,619

[22] Filed: Dec. 18, 1986

[30] Foreign Application Priority Data

Dec. 21, 1985 [DE] Fed. Rep. of Germany ....... 3545597

[51] Int. Cl.⁴ .................... A01N 43/50; C07D 413/06
[52] U.S. Cl. ......................... 71/92; 544/139; 546/210; 548/301; 548/302
[58] Field of Search ............... 548/301, 302; 544/139; 546/210; 71/92

[56] References Cited

U.S. PATENT DOCUMENTS 2,602,799  7/1952  Goldberg et al. .................. 548/301

Primary Examiner—Richard A. Schwartz
Attorney, Agent, or Firm—Weissenberger, Hammond & Littell

[57] ABSTRACT

Compounds of the formula

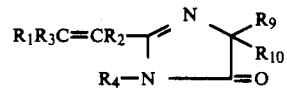

or

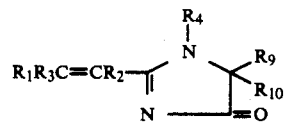

wherein $R_1$, $R_2$, $R_3$, $R_4$, $R_9$ and $R_{10}$ have diverse meanings. They are useful as herbicides.

8 Claims, No Drawings

HERBICIDAL IMIDAZOLINONES

This invention relates to novel imidazolinones, to methods of preparing these compounds, to herbicidal compositions containing them as active ingredients, and to a method of using them as herbicides.

More particularly, the present invention relates to a novel class of compounds represented by the tautomeric formulas

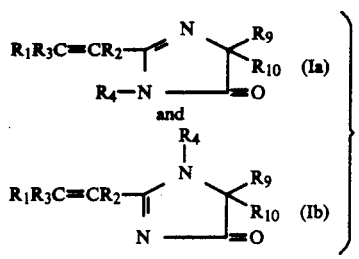

wherein
- $R_1$ and $R_2$ are each independently lower alkyl or substituted lower alkyl;
- $R_3$ is —COOR$_5$, —COR$_6$, —CN or —COOM;
- $R_4$ is hydrogen, lower alkyl, substituted lower alkyl, lower alkenyl, substituted lower alkenyl or $C_{1-4}$ alkanoyl; or
- $R_3$ and $R_4$, together with each other, are —CO—;
- $R_5$ is hydrogen, $C_{1-8}$ alkyl, substituted $C_{1-8}$ alkyl, lower alkenyl, substituted lower alkenyl, phenyl or $C_{3-7}$ cycloalkyl;
- $R_6$ is —NR$_7$R$_8$, morpholinyl, substituted morpholinyl, pyrrolidinyl, substituted pyrrolidinyl, —N-H—NH$_2$, —NH—N=CR$_{11}$R$_{12}$ or

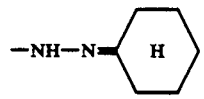

- $R_7$ is hydrogen, lower alkyl, substituted lower alkyl, lower alkenyl, phenyl, substituted phenyl, or hydroxyl;
- $R_8$ is hydrogen, lower alkyl, substituted lower alkyl, lower alkenyl, phenyl or substituted phenyl;
- $R_9$ and $R_{10}$ are each independently lower alkyl;
- $R_{11}$ is hydrogen or lower alkyl;
- $R_{12}$ is lower alkyl; and
- M is one equivalent of an alkali metal, ammonium or alkaline earth metal ion.

Suitable embodiments of the compounds of the formula I are those of the formula

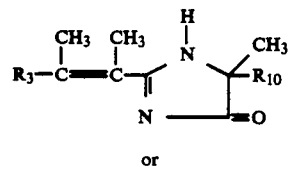

or

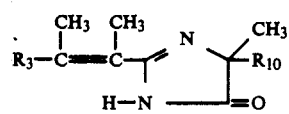

wherein $R_3$ is —COOC$_2$H$_5$, —COO—n—C$_3$H$_7$, —COO—i—C$_3$H$_7$,

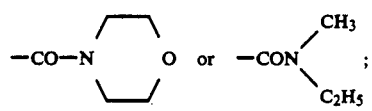

and $R_{10}$ is ethyl or isopropyl.

A preferred subgenus thereunder is constituted by imidazolinones of the tautomeric formulas

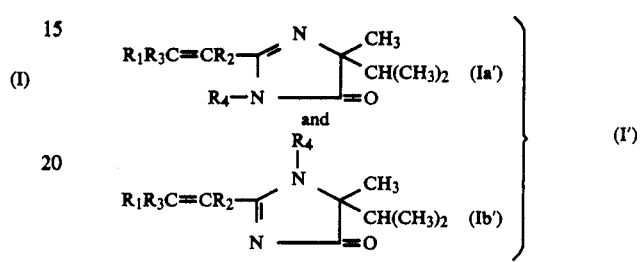

wherein
- $R_1$ and $R_2$ are each independently lower alkyl;
- $R_3$ is —COOR$_5$, —COR$_6$ or —CN;
- $R_4$ is hydrogen or $C_{1-4}$ alkanoyl; or
- $R_3$ and $R_4$, together with each other, are —CO—;
- $R_5$ is hydrogen, lower alkyl, lower alkenyl or $C_{5-7}$ cycloalkyl;
- $R_6$ is —NR$_7$R$_8$, morpholinyl, pyrrolidinyl or piperidinyl;
- $R_7$ is hydrogen, lower alkyl, phenyl or hydroxyl; and
- $R_8$ is hydrogen, lower alkyl or phenyl.

Within the scope of the above definitions, lower alkyl is preferably methyl, ethyl, n-propyl or i-propyl; alkanoyl is preferably acetyl or propionyl; and lower alkenyl is preferably allyl.

The compounds of the formulas Ia' and Ib' are derived from the tautomeric parent compounds Ia and Ib where $R_4$=H, and the 2H-pyrrolo[1,2-a]imidazoles (Ia", $R_4$ and $R_3$=—CO—) and 3H-pyrrolo[1,2-a]imidazoles (Ib", $R_4$ and $R_3$=—CO—) of the formulas

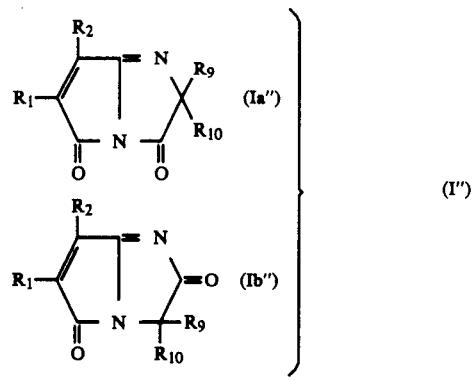

are in principle also derived from the two tautomeric basic structures Ia and Ib.

Suitable embodiments of the compounds of the formula I" are those of the formula

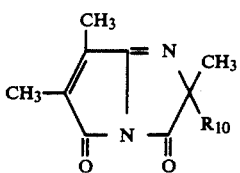

or

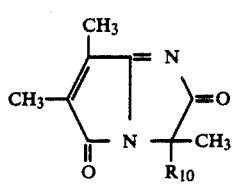

wherein $R_{10}$ is ethyl or isopropyl.

In the text which follows, formulas Ia', Ia" and Ib', Ib" and formula I, which includes the two isomers, are used depending on the particular meaning.

Preferred examples of lower alkyl groups are the $C_{1-4}$ alkyl radicals methyl, ethyl, propyl, isopropyl, n-butyl, sec.butyl, isobutyl and tert.butyl.

Preferred examples of lower alkenyl groups are $C_{2-5}$ alkenyl radicals such as vinyl and allyl.

The lower alkyl, lower alkenyl or phenyl groups according to the above definitions may be mono- or poly-substituted by halogen, alkoxy, preferably methoxy or ethoxy, hydroxy, nitro, cyano or mercapto.

The halogen substituents are fluorine, chlorine, bromine and iodine; fluorine, chlorine and bromine are preferred. Among the halogen-substituted alkyl, alkenyl and phenyl groups, particular mention should be made of trifluoromethyl, trichloromethyl, chloroalkyl, o-, m- and p-chlorophenyl and 2,4-dichlorophenyl.

Examples of substituted morpholinyl, pyrrolidinyl and piperidinyl groups include the heterocyclic compounds which are substituted up to four times by lower alkyl, halogen, hydroxy or mercapto groups.

Examples of alkali metal ions are the monovalent cations of lithium, sodium or potassium, and those of alkaline earth ions are the divalent cations iof beryllium, magnesium and calcium, preferably magnesium and calcium.

The ammonium ions are the cations obtained by protonation or alkylation of amines, such as the cations of triethanolamine, methylamine, dimethylamine, trimethylamine, ethylamine, diethylamine, triethylamine, isopropylamine or diisopropylamine.

The compounds of the formula I may be prepared by the following methods involving well known chemical synthesis principles:

Method A

By cyclizing a compound of the formula

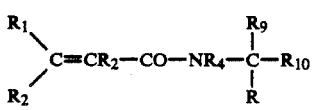
(II)

wherein $R_1$, $R_2$, $R_3$, $R_4$, $R_9$ and $R_{10}$ have the meanings previously defined, and R is —CONHR$_4$ or —CN, with the proviso that the two $R_4$ groups may have different meanings.

The cyclization is effected by using water-binding agents, for example with dicyclohexylcarbodiimide or other carbonic acid diimides, phosphorus oxychloride, phosphorus pentachloride, polyphosphoric acid, concentrated sulfuric acid or zinc chloride, all of which may also be used in the cyclization reactions referred to below, or with strong bases in the presence of $H_2O_2$. Preferably, the reaction is carried out at room temperature.

Method B

For the preparation of a compound of the formula Ia wherein $R_3$ and $R_4$ together are —CO—(Ia"), by cyclizing a compound of the formula

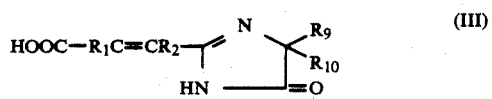
(III)

wherein $R_1$, $R_2$, $R_9$ and $R_{10}$ have the meanings previously defined in the presence of a water-binding agent such as $PCl_5$ or $POCl_3$. The water-binding agent, optionally together with an additional inert solvent, is used as the reaction medium. The reaction is preferably carried out at room temperature.

Method C

For the preparation of a compound of the formula Ib wherein $R_3$ and $R_4$ together represent —CO—(Ib"), by cyclizing a compound of the formula

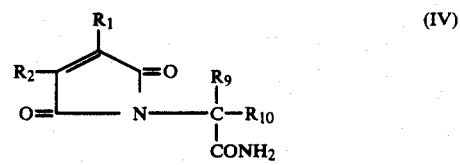
(IV)

wherein $R_1$, $R_2$, $R_9$ and $R_{10}$ have the meanings previously defined with water-binding agents or strong bases, preferably at room temperature.

Method D

For the preparation of a compound of the formula I wherein $R_4$ is H, by ring cleavage of a compound of the formula Ia" or Ib". With water or aqueous bases, a compound of the formula I is obtained wherein $R_3$ is —COOH or —COOM; with alcohols $R_5OH$, an ester is obtained (where $R_3$ is —COOR$_5$); with amines $R_6H$, an amide is obtained (where $R_3$ is —COR$_6$). The reaction is effected at temperatures between room temperature and the boiling point of the reaction mixture, optionally with the addition of a solvent which does not disrupt the reaction. From a compound where $R_3$ is —CONH$_2$, it is possible to obtain the corresponding compound where $R_3$ is —CN.

Method E

For the preparation of a compound of the formula I wherein $R_4$ has the meanings previously defined except hydrogen, by alkylating or acylating a compound of the formula

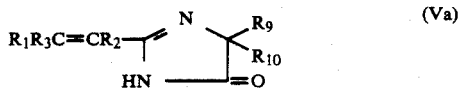
(Va)

-continued
or

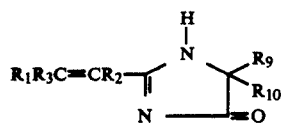  (Vb)

wherein $R_1$, $R_2$, $R_3$, $R_9$ and $R_{10}$ have the meanings previously defined, with a compound of the formula $$R_4X \quad (VI)$$

wherein $R_4$ has the meanings previously defined with the exception of hydrogen, and X is a nucleophilically exchangeable group such as halogen, p-toluenesulfonyl or mesityl, or $R_4X$ is a carboxylic acid anhydride. The reaction is generally carried out at temperatures between room temperature and the boiling point of the reaction mixture, optionally with the addition of a solvent.

Method F

For the preparation of a compound of the formula I wherein $R_3$ is $-COOR_5'$ or $-COR_6$, where $R_5'$ has the same meanings as $R_5$ with the exception of H, and $R_6$ has the meanings previously defined, a corresponding compound of the formula I wherein $R_3$ is $-COOH$ is esterified or amidated, optionally via reactive intermediate stages, with alcohols $R_5'OH$ or amines $R_6H$, or salts of these compounds.

Method G

A compound of the formula I wherein $R_3$ is $-COOM$ may be prepared from the corresponding carboxylic acid ($R_3=COOH$) by reaction with a base MOH.

If they are not already known, the starting materials for methods A to G may be obtained by conventional methods as shown in the following reaction sequences; unless otherwise stated, the substituents have the meanings previously defined.

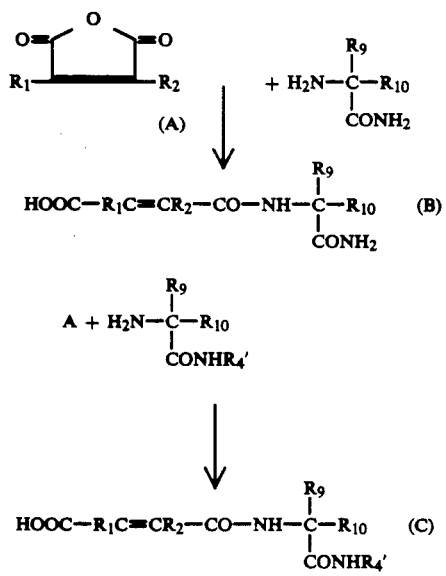

($R_4'$ equals optionally substituted lower alkyl or lower alkenyl)

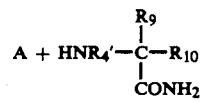

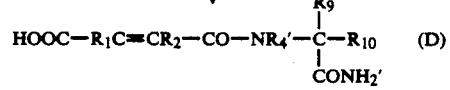

The radicals $R_1$ and $R_2$ may also occupy the reverse positions. This also applies to the other reactions described here wherein the linking may be effected in various ways. Some of the compounds of the present invention contain centers of asymmetry, so that they may occur as racemates or in the form of enantiomers. Cyclization of compounds (B) leads to compounds III. Starting materials of the formula IV are obtained according to the following reaction sequence:

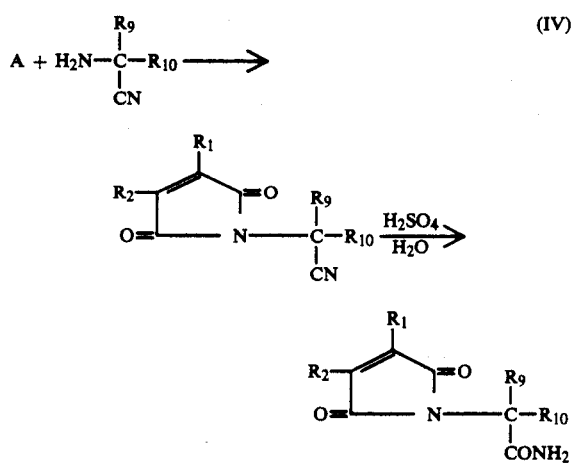

Cyclization of C leads to compounds of the formula

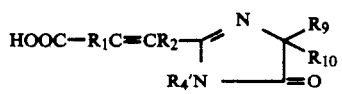

and cyclization of D yields compounds of the formula

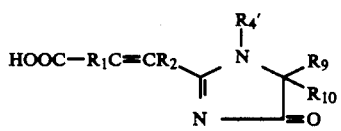

In both cases, these are end products of the formula I which in turn constitute starting materials for end products with a modified carboxyl group.

In order to prepare an ester of the formula II wherein $R_3$ is $-COOR_5'$ and $R_1$, $R_2$, $R_5'$, $R_9$ and $R_{10}$ have the meanings previously defined, a corresponding acid of the formula II wherein $R_3$ is $-COOH$ is reacted in the presence of catalytic quantities of a strong acid, such as p-toluene-sulfonic acid, in an excess of an alcohol $R_5'OH$ while heating.

The following examples illustrate the present invention and will enable others skilled in the art to understand it more completely. It should be understood, however, that the invention is not limited solely to the particular examples given below.

EXAMPLE 1

2-(2-Carboxy-1-methyl-prop-1-enyl)-4-isopropyl-4-methyl-4H-imidazol-1(3)H-5-one (a) 2,3-Dimethyl-N-(1-aminocarbonyl-1,2-dimethylpropyl)maleic acid monoamide (II)

A mixture of 46 g of dimethylmaleic acid anhydride, 48 g of 2-amino-2,3-dimethylbutyric acid amide and 70 ml of methylene chloride was heated at its boiling point for 15 minutes. After some of the solvent had been distilled off, the residual mixture was stirred with 300 ml of diethyl ether, and the product precipitated thereby was suction-filtered off. The desired compound (II) (90 g; 96%) was isolated as a crystalline solid, melting point 70°–72° C.

(b) 34.6 g of 2,3-dimethyl-N-(1-aminocarbonyl-1,2-dimethylpropyl)-maleic acid monoamide (II) were suspended in 150 ml of acetonitrile, 30.9 g of bicyclohexyl carboxylic acid diimide were added, and the mixture was stirred at room temperature for 3 days. The urea precipitated thereby was filtered off, the filtrate was concentrated by evaporation and purified on silica gel with acetone/heptane (1:1). The title compound (27.4 g; 86%) was isolated in the form of colorless crystals, m.p. 126°–9° C.

Advantageously, the reaction sequence (a)/(b) is carried out as a one-pot reaction without isolation of the first stage.

The salts may be prepared from the resulting carboxylic acid of the formula I as follows:

EXAMPLE 2

2-(2-Carboxy-1-methyl-propyl-1-enyl)-4-isopropyl-4-methyl-4H-imidazole-1(3)H-5-one ammonium salt 2-(2-Carboxy-1-methyl-prop-1-enyl)-4-isopropyl-4-methyl-4H-imidazole-1(3)H-4-one was reacted in aqueous methanolic solution with an equimolar quantity of ammonia to yield a solution of the desired salt of the title compound.

Analogous to Example 2, the following salts were prepared in aqueous methanolic solution by reaction with the corresponding base:

(a) 2-(Carboxy-1-methyl-prop-1-enyl)-4-isopropyl-4-methyl-4H-imidazole-1(3)H-5-one isopropylammonium salt (b) 2-(Carboxy-1-methyl-prop-1-enyl)-4-isopropyl-4-methyl-4H-imidazole-1(3)H-5-one isopropyldimethylammonium salt (c) 2-(Carboxy-1-methyl-prop-1-enyl)-4-isopropyl-4-methyl-4H-imidazole-1(3)H-5-one diethylammonium salt (d) 2-(Carboxy-1-methyl-prop-1-enyl)-4-isopropyl-4-methyl-4H-imidazole-1(3)H-5-one triethylammonium salt (e) 2-(Carboxy-1-methyl-prop-1-enyl)-4-isopropyl-4-methyl-4H-imidazole-1(3)H-5-one n-hexylammonium salt (f) 2-(Carboxy-1-methyl-prop-1-enyl)-4-isopropyl-4-methyl-4H-imidazole-1(3)H-5-one sodium salt (g) 2-(Carboxy-1-methyl-prop-1-enyl)-4-isopropyl-4-methyl-4H-imidazole-1(3)H-5-one calcium salt (h) 2-(Carboxy-1-methyl-prop-1-enyl)-4-isopropyl-4-methyl-4H-imidazole-1(3)H-5-one [tri-(2-hydroxyethyl)]-ammonium salt

EXAMPLE 3

2-Isopropyl-2,6,7-trimethyl-2H-pyrrolo[1,2-a]-imidazole-3,5-dione (Ia)

2.38 g of 2-(2-carboxy-1-methyl-prop-1-enyl)-4-isopropyl-4-methyl-4H-imidazole-1(3)H-5-one were stirred in 5 ml of $POCl_3$ with 2.09 g of $PCl_5$. A dark solution was formed which was concentrated by evaporation after standing for some time. The residue was stirred with chloroform/ice water, and the organic phase was separated, evaporated and purified by chromatography. The title compound was isolated in the form of an oil which solidified upon trituration; M.p. 98°–99° C. (1.55 g; 70%).

Elemental analysis: Calculated: C: 65.45% H: 7.27% N: 12.73%; Found: C: 63.96% H: 7.64% N: 12.76%.

EXAMPLE 4

3-Isopropyl-3,6,7-trimethyl-3H-pyrrolo[1,2-a]-imidazole-2,5-dione (Ib)

4.5 g of 1-(1-aminocarbonyl-2,3-dimethyl-propyl)-3,4-dimethyl-pyrrole-2,5-dione were suspended in 8 ml of $POCl_3$ and 4.5 g of $PCl_5$ were added in batches. The mixture was stirred for 2 hours at room temperature, concentrated by evaporation, the residue was taken up in chloroform/ice water, and the organic phase was separated and purified on silica gel with acetone/heptane (1:1).

The title compound was isolated in the form of a yellow oil (3.3 g; 79%).

Elemental analysis: Calculated: C: 65.45% H: 7.27% N: 12.73%; Found: C: 63.93% H: 7.24% N: 12.26%.

EXAMPLE 5

2-[2-(Morpholin-4-yl-carbonyl)-1-methyl-prop-1-enyl]-4-methyl-4-isopropyl-4H-imidazole-1(3)H-5-one A mixture of 5 ml of morpholine, 2.2 g of 3-isopropyl-3,6,7-trimethyl-3H-pyrrolo[1,2-a]imidazole-2,5-dione (Ib″) and 10 ml of acetonitrile was heated at its boiling point for 30 hours. After the reaction mixture had been concentrated by evaporation the residue was purified on silica gel with acetone/heptane (1:1).

The title compound was isolated as a light brown oil (1.7 g).

Elemental analysis: Calculated: C: 62.60% H: 8.15% N: 13.70%; Found: C: 62.28% H: 8.31% N: 13.28%.

EXAMPLE 6

2-(2-Carboxy-1-ethyl-prop-1-enyl)-4-isopropyl-4-methyl-4H-imidazole-1(3)H-5-one (I)

and 2-(2-Carboxy-1-methyl-but-1-enyl)-4-isopropyl-4-methyl-4H-imidazole-1(3)H-5-one (I)

31 ml of a 1.6 molar solution of butyl lithium in hexane was added dropwise over a period of 2 hours at −15° C. to a solution of 7.0 g of ethyl methyl maleic acid anhydride and 6.7 g of 2-amino-2,3-dimethylbutyric acid nitrile in tetrahydrofuran, the mixture was stirred for 30 minutes at 0° C., and then 13 g of an aqueous 50% sodium hydroxide solution followed by 30 ml of water were added. The organic phase was separated and 24 g of 30% perhydrol were added dropwise over a period of 45 minutes at −10° C. The mixture was stirred for 3 hours at 80° C., then neutralized with sulfuric acid and extracted with dichloromethane. A yellow oil was isolated from the organic phase, which crystallized out when stirred with ether.

A mixture of the title compounds (0.9 g) was isolated in the form of white crystals, m.p. 155°-157° C. The compound may also be prepared as described in Example 1(a)/1(b).

EXAMPLE 7

2-(2-Ethoxycarbonyl-1-methyl-prop-1-enyl)-4-isopropyl-4-methyl-4H-imidazole-1(3)H-5-one (I)

(a) 2,3-Dimethyl-N-(1-aminocarbonyl-1,2-dimethylpropyl)maleic acid monoamide ethyl ester (II).

The desired compound (II) (5.5 g; 97%) was isolated after heating 4.76 g of 2-(2-carboxy-1-methyl-prop-1-enyl-4-isopropyl-4-methyl-4H-imidazole-1(3)H-5-one (I) in 50 ml of ethanol for several hours in the presence of catalytic quantities of p-toluene-sulfonic acid. The product was obtained in the form of colorless crystals, m.p. 113°-116° C.

(b) 4.3 g of 2,3-dimethyl-N-(1-aminocarbonyl-1,2-dimethylpropyl)-maleic acid monoamide ethyl ester (II) were suspended in 6 ml of $POCl_3$, 3.1 g of $PCl_5$ were added, and the mixture was stirred for 1 hour at room temperature, concentrated by evaporation, poured over ice, mixed with dichloromethane, neutralized with sodium bicarbonate, and the organic phase was isolated, dried and evaporated. The residue was purified on silica gel with acetone/heptane (1:1).

The title compound (1.3 g; 33%) was isolated in the form of colorless crystals, m.p. 98°-100° C.

EXAMPLE 8

2-(2-Carbamyl-1-methyl-prop-1-enyl)-4-isopropyl-4-methyl-4H-imidazole-1(3)H-5-one (I)

2.66 g of 2-isopropyl-2,6,7-trimethyl-2H-pyrrolo[1,2-a]imidazole-3,5-dione were heated at 80° C. for 10 hours in an autoclave with ammonia in tetrahydrofuran (about 20 ml of liquid ammonia in 30 ml of tetrahydrofuran). The reaction mixture was then filtered, the filtrate was evaporated, and the residue was triturated with diethyl ether.

The title compound (2.4 g) was isolated in the form of brownish crystals, m.p. 187°-191° C.

EXAMPLE 9

2-(1-Methyl-2-morpholinocarbonyl-prop-1-enyl-4-isopropyl-4-methyl-4H-imidazole-1(3)H-5-one

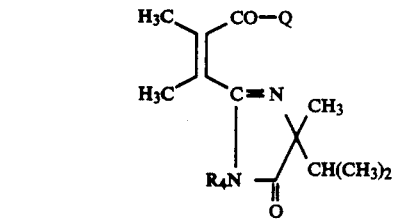

(Z)

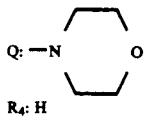

$R_4$: H 2.4 g of 2-isopropyl-2,6,7-trimethyl-2H-pyrrolo-[1,2-a]-imidazole-3,5-dione were added to a solution of 14.3 g of morpholine in 150 ml of absolute methanol, and the mixture was refluxed for 2 hours. The mixture was then evaporated down to about 60 g, diluted with ether, suction-filtered, and the filter cake was washed with ether and dried.

26.6 g (80% of theory) of a white crystalline product were obtained, m.p. 174°-175° C.

EXAMPLE 10

2-(2-Hydrazinocarbonyl-1-methylprop-1-enyl)-4-isopropyl-4-methyl-4H-imidazole-1(3)H-5-one (Formula Z; Q: —NH—$NH_2$, $R_4$: H)

5.4 g of 2-isopropyl-2,6,7-trimethyl-2H-pyrrolo-[1,2-a]imidazole-3,5-dione were added to a solution of 1.23 g of hydrazine hydrate in 50 ml of methanol. The mixture was stirred for a quarter of an hour at room temperature and then evaporated. The residue was dissolved in ether, crystallized, suction-filtered, washed and dried. 5.8 g (94% of theory) of a white crystalline substance were obtained, m.p. 163°-165° C.

EXAMPLE 11

2-(1-Methyl-2-n-propoxycarbonylprop-1-enyl)-1-acetyl-4-isopropyl-4-methyl-4H-imidazole-1H-5-one (Formula Z; Q: —O—n—$C_3H_7$, $R_4$: —$CH_3CO$)

2.8 g of 1-(1-methyl-2-n-propoxycarbonylprop-1-enyl)-4-isopropyl-4-methyl-4H-imidazole-1H-5-one were refluxed for 5 hours in 30 ml of acetic anhydride. The mixture was then evaporated, and the residue was chromatographed on silica gel with 800 ml of acetone/heptane 1:1. 2.8 g (87% of theory) of a yellow oil were obtained.

Elemental analysis: Calculated: C: 63.30% H: 8.07% N: 8.69%; Found: C: 61.95% H: 8.24% N: 8.77%.

The corresponding ethyl ester (formula Z; Q: —$OC_2H_5$; $R_4$: —$CH_3CO$) was obtained analogously. Oil: yield: 88% of theory.

EXAMPLE 12

2-(2-Ethylenehydrazocarbonyl-1-methylprop-1-enyl)-4-isopropyl-4-methyl-4H-imidazole-1-(3)H-5-one (Formula Z: Q: —NH—N=CH—$CH_3$, $R_4$: H)

A mixture of 2.2 g of the product obtained in Example 10 and 30 ml of methanol was mixed with 2.2 g of acetaldehyde. The mixture was allowed to stand for half an hour at room temperature, evaporated, crystallized with 30 ml of ether, suction-filtered and dried. 2.1 g (87% of theory) of white crystals were obtained, m.p. 173°-174° C.

The following compounds of the formula Z: ($R_4$=H) were obtained analogously:

| Q | M.p. [°C.] |
| --- | --- |
| —NH—N=$C(CH_3)_2$ | 158-161 |
| —NH—N=⟨H⟩(phenyl) | 163-166 |

EXAMPLE 13

2-(2-Ethoxycarbonyl-1-methylprop-1-enyl)-4-isopropyl-4-methyl-4H-imidazole-1(3)H-5-one

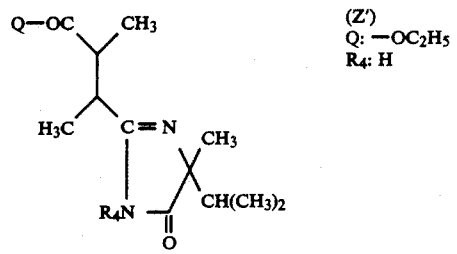

(Z')
Q: —OC$_2$H$_5$
R$_4$: H

A solution of 13 g of monoethyl 2,3-dimethylfumarate chloride in 20 ml of methylene chloride was added dropwise, while stirring and cooling with ice, to a solution of 12 g of 2-amino-2,3-dimethyl-butyric acid amide and 12 ml of triethylamine in 80 ml of methylene chloride. The mixture was stirred for 2 hours at room temperature, the resulting solution was extracted with water, with 2N hydrochloric acid and again with water, then dried and evaporated. The residue was triturated with diethyl ether, suction-filtered and recrystallized from a little ethanol. 8.0 g (41% of theory) of monoethyl-2,3-dimethylfumarate-N-(1-aminocarbonyl-1-methylisobutyl)-amide were obtained, m.p. 122°–125° C.

8.0 g of this compound were added to a mixture of 10 g of PCl$_5$ and 50 ml of POCl$_3$, and the resulting mixture was stirred for 6 hours at room temperature. The mixture was evaporated in vacuo at 60° C., the residue was taken up in methylene chloride, stirred with water and neutralized with sodium bicarbonate. The methylene chloride solution was separated, dried and evaporated. 7.0 g (93% of theory) of a light yellow oil were obtained, the structure of which was confirmed by spectroscopy.

EXAMPLE 14

2-(1-Methyl-2-morpholinocarbonylprop-1-enyl)-4-isopropyl-4-methyl-4H-imidazole-1(3)H-5-one (Formula Z'; Q: 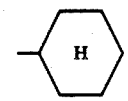, R$_4$: H)

3.7 g of the end product of Example 13 were stirred with 4 ml of morpholine for 2 hours at 120° C. The excess morpholine was distilled off in vacuo, and the residue was purified chromatographically (80 g of silica gel, diisopropyl ether/methanol 10:3). 1.7 g of oily residue were obtained from which the reaction product, m.p. 145° C., was isolated by trituration with ether.

The Tables which follow list other compounds which were prepared according to the invention:

TABLE I

Compounds of the formula

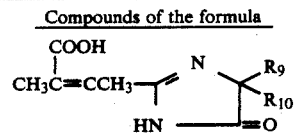

| Example No. | R$_9$ | R$_{10}$ | M.p. [°C.] |
|---|---|---|---|
| 15 | CH$_3$ | CH$_3$ | 150–158 |
| 16 | CH$_3$ | C$_2$H$_5$ | 113–115 |
| 17 | C$_2$H$_5$ | C$_2$H$_5$ | 135–140 |
| 18 | CH$_3$ | n-C$_3$H$_7$ | 116–118 |

TABLE II

Compounds of the formula

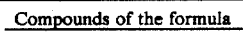

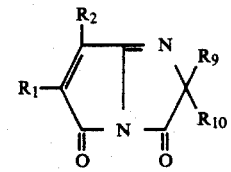

| Example No. | R$_1$ | R$_2$ | R$_9$ | R$_{10}$ | M.p. [°C.] |
|---|---|---|---|---|---|
| 19 | CH$_3$ | CH$_3$ | CH$_3$ | CH$_3$ | 100–103 |
| 20 | CH$_3$ | CH$_3$ | CH$_3$ | C$_2$H$_5$ | 88–89 |
| 21 | CH$_3$ | CH$_3$ | CH$_3$ | n-C$_3$H$_7$ | 68–70 |
| 22 | CH$_3$ | CH$_3$ | C$_2$H$_5$ | C$_2$H$_5$ | 75–78 |
| 23* | CH$_3$ | C$_2$H$_5$ | CH$_3$ | i-C$_3$H$_7$ | Oil |

*Substituents R$_1$ and R$_2$ may also be arranged in the opposite configuration, i.e. R$_1$ = C$_2$H$_5$, R$_2$ = CH$_3$.

TABLE III

Compounds of the formula

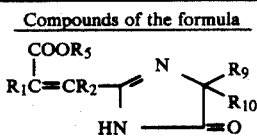

| Example No. | R$_1$ | R$_2$ | R$_5$ | R$_9$ | R$_{10}$ | M.p. [°C.] |
|---|---|---|---|---|---|---|
| 24 | CH$_3$ | CH$_3$ | C$_2$H$_5$ | CH$_3$ | CH$_3$ | |
| 25 | CH$_3$ | CH$_3$ | C$_2$H$_5$ | CH$_3$ | C$_2$H$_5$ | 95 |
| 26 | CH$_3$ | CH$_3$ | CH$_3$ | CH$_3$ | i-C$_3$H$_7$ | 128–131 |
| 27 | CH$_3$ | CH$_3$ | C$_2$H$_5$ | CH$_3$ | i-C$_3$H$_7$ | 100–101 |
| 28 | CH$_3$ | CH$_3$ | n-C$_3$H$_7$ | CH$_3$ | i-C$_3$H$_7$ | 84–85 |
| 29 | CH$_3$ | CH$_3$ | i-C$_3$H$_7$ | CH$_3$ | i-C$_3$H$_7$ | 85–87 |
| 30 | CH$_3$ | CH$_3$ | n-C$_4$H$_9$ | CH$_3$ | i-C$_3$H$_7$ | 82–83 |
| 31 | CH$_3$ | CH$_3$ | CH$_2$—CH$_2$—CH(CH$_3$)$_2$ | CH$_3$ | i-C$_3$H$_7$ | 80–83 |
| 32 | CH$_3$ | CH$_3$ | n-C$_8$H$_{17}$ | CH$_3$ | i-C$_3$H$_7$ | |
| 33 | CH$_3$ | CH$_3$ | —⟨H⟩ (cyclohexyl) | CH$_3$ | i-C$_3$H$_7$ | 113–117 |
| 34 | CH$_3$ | CH$_3$ | C$_2$H$_5$ | CH$_3$ | n-C$_3$H$_7$ | 88–90 |
| 35 | CH$_3$ | CH$_3$ | C$_2$H$_5$ | C$_2$H$_5$ | C$_2$H$_5$ | |
| 36* | CH$_3$ | C$_2$H$_5$ | CH$_3$ | CH$_3$ | i-C$_3$H$_7$ | Oil |
| 37* | CH$_3$ | C$_2$H$_5$ | C$_2$H$_5$ | CH$_3$ | i-C$_3$H$_7$ | Oil |
| 38* | CH$_3$ | C$_2$H$_5$ | n-C$_3$H$_7$ | CH$_3$ | i-C$_3$H$_7$ | Oil |

*Isomers were obtained, i.e. R$_1$ could also be C$_2$H$_5$ and R$_2$ could be CH$_3$.

TABLE IV

Compounds of the formula $$R_1C=CR_2-C(CONR_7R_8)=N-C(R_9)(R_{10})-C(=O)-NH-$$
(cyclic imidazolinone structure)

| Example No. | $R_1$ | $R_2$ | $R_7$ | $R_8$ | $R_9$ | $R_{10}$ | M.p. [°C.] |
|---|---|---|---|---|---|---|---|
| 39 | $CH_3$ | $CH_3$ | H | OH | $CH_3$ | $i\text{-}C_3H_7$ | 174–175 |
| 40 | $CH_3$ | $CH_3$ | H | $C_2H_5$ | $CH_3$ | $i\text{-}C_3H_7$ | 197–200 |
| 41 | $CH_3$ | $CH_3$ | H | $i\text{-}C_3H_7$ | $CH_3$ | $i\text{-}C_3H_7$ | 218–221 |
| 42 | $CH_3$ | $CH_3$ | H | $n\text{-}C_6H_{13}$ | $CH_3$ | $i\text{-}C_3H_7$ | 184–186 |
| 43 | $CH_3$ | $CH_3$ | H | –C₆H₁₁ (cyclohexyl) | $CH_3$ | $i\text{-}C_3H_7$ | 225–230 |
| 44 | $CH_3$ | $CH_3$ | H | $C_6H_5$ | $CH_3$ | $i\text{-}C_3H_7$ | 240–243 |
| 45 | $CH_3$ | $CH_3$ | $CH_3$ | $CH_3$ | $CH_3$ | $i\text{-}C_3H_7$ | 160–162 |
| 46 | $CH_3$ | $CH_3$ | $C_2H_5$ | $C_2H_5$ | $CH_3$ | $i\text{-}C_3H_7$ | 145–146 |
| 47 | $CH_3$ | $CH_3$ | $CH_2\text{-}CH=CH_2$ | $CH_2\text{-}CH=CH_2$ | $CH_3$ | $i\text{-}C_3H_7$ | 142–143 |
| 48 | $CH_3$ | $CH_3$ | $-(CH_2)_4-$ | | $CH_3$ | $i\text{-}C_3H_7$ | 159–161 |
| 49 | $CH_3$ | $CH_3$ | $-CH_2-CH_2-O-CH_2-CH_2-$ | | $CH_3$ | $CH_3$ | 158–160 |
| 50 | $CH_3$ | $CH_3$ | H | $CH(CH_3)_2$ | $CH_3$ | $C_2H_5$ | 170–175 |
| 51 | $CH_3$ | $CH_3$ | $-CH_2-CH_2-O-CH_2-CH_2-$ | | $CH_3$ | $C_2H_5$ | 158–160 |
| 52 | $CH_3$ | $CH_3$ | $-CH_2-CH_2-O-CH_2-CH_2-$ | | $C_2H_5$ | $C_2H_5$ | 167–170 |
| 53* | $CH_3$ | $C_2H_5$ | H | $CH_3$ | $CH_3$ | $i\text{-}C_3H_7$ | 161–165 |
| 54* | $CH_3$ | $C_2H_5$ | $-CH_2-CH_2-O-CH_2-CH_2-$ | | $CH_3$ | $i\text{-}C_3H_7$ | 127–130 |

*Isomers were obtained, i.e. $R_1$ may also be $C_2H_5$ and $R_2$ may be $CH_3$.

TABLE A

Starting materials of the formula $$R_3'O-CO-C(CH_3)=C(CH_3)-CONH-C(CH_3)(CONH_2)-CH(CH_3)_2$$

| No. | $R_3'$ | M.p. [°C.] |
|---|---|---|
| 1 | $C_2H_5$ | 117–118 |
| 2 | $n\text{-}C_3H_7$ | 125–126 |
| 3 | $i\text{-}C_3H_7$ | 124–126 |
| 4 | $n\text{-}C_4H_9$ | 115–116 |
| 5 | $CH_2CH_2CH(CH_3)_2$ | 79–80 |
| 6 | $n\text{-}C_8H_{17}$ | 84–85 |
| 7 | $CH_2CH=CH_2$ | |
| 8 | $CH_2CH_2-O-C_2H_5$ | 52–60 |
| 9 | –C₆H₁₁ (cyclohexyl) | 129–130 |

TABLE B

Starting materials of the formula $$R_3'-CO-R_1C=CR_2-CONH-C(R_9)(R_{10})-CONH_2$$

| No. | $R_1$ | $R_2$ | $R_9$ | $R_{10}$ | $R_3'$ | M.p. [°C.] |
|---|---|---|---|---|---|---|
| 1 | $CH_3$ | $CH_3$ | $CH_3$ | $CH_3$ | $C_2H_5$ | |
| 2 | $CH_3$ | $CH_3$ | $CH_3$ | $C_2H_5$ | $C_2H_5$ | 142–145 |
| 3 | $CH_3$ | $CH_3$ | $CH_3$ | $n\text{-}C_3H_7$ | $C_2H_5$ | 138 |
| 4 | $CH_3$ | $CH_3$ | $C_2H_5$ | $C_2H_5$ | $C_2H_5$ | 150 |
| 5 | $CH_3$ or $C_2H_5$ | $C_2H_5$ or $CH_3$ | $CH_3$ | $i\text{-}C_3H_7$ | $CH_3$ | 65–67 |
| 6 | $CH_3$ or $C_2H_5$ | $C_2H_5$ or $CH_3$ | $CH_3$ | $i\text{-}C_3H_7$ | $CH_3$ | 68–70 |
| 7 | $CH_3$ | $C_2H_5$ | $CH_3$ | $i\text{-}C_3H_7$ | $CH_3$ | 75 |

The compounds of the present invention have useful properties. More particularly, they exhibit selective herbicidal activity.

Numerous 2-phenyl- or 2-hetaryl-substituted 4-isopropyl-4-methyl-4H-imidazole-1(3)H-5-ones are already known. These compounds exhibit herbicidal activity. However, they are not always satisfactory in terms of their potency, activity profile and toxicity.

Compared with them, the compounds of the formula I exhibit significantly better herbicidal activity.

The herbicidal activity of the compounds of the present invention was ascertained as follows:

The damage to weeds as well as the compatibility with cultivated plants was evaluated on a scale from 1–9.

| In this scale | |
|---|---|
| 1 | indicates 100% |
| 2 | indicates 100–97.5% |
| 3 | indicates 97.5–95% |
| 4 | indicates 95–90% |
| 5 | indicates 90–85% |
| 6 | indicates 85–75% |
| 7 | indicates 75–65% |
| 8 | indicates 65–32.5% |
| 9 | indicates 32.5–0% activity. |

1. Activity on weeds

Seeds or parts of the rhizome of mono- and dicotyledonous weeds were placed in uniform soil in plastic pots (9 cm diameter) and covered with sand. The compounds of this invention, formulated as wettable powders or as emulsifiable concentrates, were applied to the top of the sand in the form of aqueous suspensions or emulsions. The quantity of water used per pot corresponded to about 800 liters per hectare. After treatment, the test pots were placed in the greenhouse, and the test plants were cultivated under good growth conditions (temperature: 20° C. by day, 15° C. by night, relative humidity 60–80%). After about 3 weeks the damage to the plants was evaluated visually. Untreated controls were used as a comparison.

The compounds of the present invention had a herbicidal activity which was excellent in some cases against economically significant mono and dicotyledonous weeds.

Similarly, various weeds were grown in pots in the greenhouse to the 2- to 6-leaf stage and then treated with the compounds of the invention by the post-emergence method. After about 3 to 4 weeks, the test plants were assessed visually and the damage was evaluated.

The compounds of the invention, such as those of Examples 1, 2, (2c) and 3, also proved to be very effective in this test.

17. Test for growth-regulating activity Inhibition of growth in cereal

In dish tests in the greenhouse, young cereal plants (wheat, barley and rye) at the 3-leaf stage were sprayed with the test compounds until dripping wet. After the untreated control plants had attained a height of about 55 cm, the growth of all the plants was measured and the inhibition of growth was calculated as a percentage of the growth of the control plants. The phytotoxic activity of the compounds was also observed. The compounds, such as those in Examples 1, 2, (2c) and 3 also proved to be very effective.

The invention thus further relates to novel herbicidal compositions containing at least one compound of the formula I as an active ingredient, as well as to methods of controlling weeds therewith.

The compounds of the formula I may be used in unaltered form or preferably as compositions with excipients conventionally used for formulation, for example as emulsifiable concentrates, wettable powders, soluble powders, dusting powders, granules or directly sprayable solutions.

Compositions containing an active ingredient of the formula I are prepared by known methods of formulation, such as by mixing or grinding with diluents and, if desired, other adjuvants.

Examples of diluents and adjuvants include solvents, solid carriers and optionally surface-active compounds.

Examples of suitable solvents include: Aromatic hydrocarbons, preferably the fractions $C_8$ to $C_{12}$, such as xylene mixtures or substituted naphthalenes; phthalic acid esters such as dibutyl or dioctyl phthalate; aliphatic hydrocarbons such as cyclohexane or paraffins; alcohols and glycols and the ethers and esters thereof, such as methanol, ethanol, propanol, isopropanol, ethylene glycol, ethylene glycol monomethyl or ethyl ether; ketones such as cyclohexanone; strongly polar solvents such as N-methyl-2-pyrrolidone, dimethylsulfoxide or dimethylformamide; optionally epoxidized vegetable oils such as epoxidized coconut oil or soybean oil; or water.

Solid carriers, for instance for dusting powders and dispersible powders, are generally natural powdered rock, such as calcite, talc, kaolin, montmorillonite or attapulgite. In order to improve the physical properties, highly dispersed silica or other artificial or natural polymers such as methyl cellulose or ethyl cellulose may also be added.

Surface-active compounds may be non-ionic, cationic and/or anionic surfactants with good emulsifying, dispersing and wetting properties, depending on the nature of the active substance of the formula I which is to be formulated. The term "surfactants" also includes surfactant mixtures.

Suitable anionic surfactants may be both so-called water-soluble soaps and water-soluble synthetic surface-active compounds.

Examples of soaps include the alkali metal, alkaline earth metal or optionally substituted ammonium salts of higher fatty acids ($C_{10-22}$), such as the Na or K salts of oleic or stearic acid, or of natural fatty acid mixtures which may be obtained, for example, from coconut or tallow oil. The methyl taurin salts of fatty acids should also be mentioned. However, more frequently, synthetic surfactants are used, especially fatty sulfonates, fatty sulfates, sulfonated benzimidazole derivatives or alkyl aryl sulfonates.

The fatty sulfates or sulfonates are generally obtained as alkali metal, alkaline earth metal or optionally substituted ammonium salts and have an alkyl group with 8 to 22 carbon atoms, where the term "alkyl" also includes the alkyl moiety of acyl groups, for instance, the Na or Ca salt of lignin sulfonic acid, dodecylsulfuric acid ester or a fatty alcohol sulfate mixture prepared from natural fatty acids.

Examples of alkyl aryl sulfonates include the Na, Ca or triethanolamine salts of dodecylbenzenesulfonic acid, dibutyl naphthalene sulfonic acid or a naphthalene-sulfonic acid/formaldehyde condensation product.

It is also possible to use corresponding phosphates such as salts of the phosphoric acid ester of a p-nonyl-(4–14)ethylene oxide adduct or phospholipids.

Primary examples of non-ionic surfactants include polyglycol ether derivatives of aliphatic or cycloaliphatic alcohols, saturated or unsaturated fatty acids and alkyl phenols.

Examples of non-ionic surfactants include nonylphenol polyethoxyethanols, castor oil polyglycol ether, polypropylene-polyethylene oxide adducts, tributylphenoxy-polyethoxyethanol, polyethyleneglycol and octylphenoxy-polyethoxyethanol.

The surfactants commonly used in formulations are described, inter alia, in the following publication: "McCutcheon's Detergents and Emulsifiers Annual", MC Publishing Corporation, Ridgewood, N.J., 1981.

The herbicidal and growth-regulating compositions of the instant invention generally contain 0.1 to 95%, particularly 0.1 to 80% of an active ingredient of the formula I, 1 to 99.9% of a solid or liquid additive and 0 to 25%, particularly 0.1 to 25%, of a surfactant. If desired, the compositions are diluted with water in order to prepare spray liquors.

In particular, the preferred compositions have the following formulations (%=percent by weight).

Emulsifiable concentrates:

| | |
|---|---|
| Compound of the formula I: | 1 to 25%, preferably 5 to 10% |

-continued

| | |
|---|---|
| Surfactant: | 5 to 30%, preferably 10 to 20% |
| Liquid carrier: | q.s. ad 100% |
| Dusting powders: | |
| Compound of the formula I: | 0.1 to 10%, preferably 0.1 to 1% |
| Solid carrier: | q.s. ad 100% |
| Suspension concentrates: | |
| Compound of the formula I: | 5 to 75%, preferably 10 to 50% |
| Surfactant: | 1 to 40%, preferably 2 to 30% |
| Water or water/alcohol: | q.s. ad 100% |
| Wettable powder: | |
| Compound of the formula I: | 0.5 to 95% |
| Surfactant: | 0.5 to 20%, preferably 1 to 15% |
| Solid carrier: | q.s. ad 100% |
| Granules: | |
| Compound of the formula I: | 0.5 to 30%, preferably 3 to 15% |
| Solid carrier: | q.s. ad 100% |

Whereas concentrated compositions are preferred as the retail form, the ultimate user generally uses diluted compositions. The concentrated compositions may be diluted to give an active ingredient concentration of only 0.001%. The quantities applied are generally from 0.01 to 10 kg active ingredient/hectare, preferably 0.025 to 5 kg active ingredient/hectare.

Examples of Concentrated Compositions (%=percent by weight)

(1) Dusting powder
  0.3% compound of the formula I
  1.0% methylcellulose
  98.7% talc
(2) Wettable powder
  25% compound of the formula I
  55% kaolin
  10% colloidal silica
  9% calcium lignin sulfonate
  1% sodium tetrapropylene benzosulfonate
(3) Wettable powder
  95% compound of the formula I
  4% calcium lignin sulfonate
  1% sodium tetrapropylene benzosulfonate
(4) Emulsifiable concentrate
  10% compound of the formula I
  80% dimethylformamide
  6.5% Tensiofix AS (emulsifier)
  3.5% Tensiofix DS (emulsifier)
(5) Suspension concentrate
  20% compound of the formula I
  3% dispersant, such as the Na salt of naphthalene-sulfate-aldehyde copolymer
  1% bentone EW (montmorillonite)
  0.2% anti-foamer (silicon)
  0.5% preservative
  q.s. ad 100% water Spray liquors are prepared from concentrates (2) and (4) by mixing with water and generally contain between 0.05 and 0.5% of active substance.

The herbicidal compounds or compositions of the instant invention may be used as defoliants, desiccants or weed killers or as growth-regulators. The term "weeds" is used herein in its broadest sense to indicate any plants growing where they are not wanted.

The activity of the compounds of the present invention as total or selective herbicides or as growth regulators depends essentially on the quantity applied, the type of treatment, the time of treatment and the formulation.

The active substances according to the present invention may be used, for example, on the following plants, but the list should not be taken as a restriction of the application to the genera mentioned.

Dicotyledonous weeds of the genera

Sinapis, Lepidium, Galium, Stellaris, Matricaria, Anthemis, Galinsoga, Chenopodium, Urtica, Senecio, Amaranthus, Portulaca, Xanthium, Convolvulus, Ipomoea, Polygonum, Sesbanis, Ambrosia, Cirsiu, Carduus, Sonchus, Solanum, Rorippa, Rotala, Lindernia, Lamium, Veronica, Abutilon, Emex, Datura, Viola, Galeopsis, Papaver, Centaurea.

Dicotyledonous crops of the genera

Gossypium, Glycine, Beta, Daucus, Phaseolus, Pisum, Solanum, Linum, Ipomoea, Vicia, Nicotiana, Lycopersicon, Arachis, Brassica, Lactura, Cucumis, Cucurbita.

Monocotyledonous weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischeamum, Sphenoclea, Dactyloctenium, Agrostis, Alopercurus, Apera.

Monocotyledonous crops of the genera

Oryza, Zea, Triticum, Hordeum, Avena, Secale, Sorghum, Panicum, Saccharum, Ananas, Asperagus, Allium.

The herbicidal compounds of this invention may be used both pre- and post-emergence on useful crops such as wheat, cotton, soybeans or potatoes, or in long-term cultivations, for instance in forestry or on ornamental trees, in fruit orchards, vineyards and hops or berry fields.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

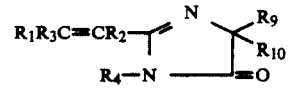

or

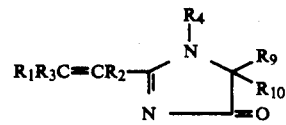

wherein
$R_1$ and $R_2$ are each independently lower alkyl;
$R_3$ is —COOR$_5$, —COR$_6$, —CN or —COOM;

$R_4$ is hydrogen, lower alkyl, lower alkenyl, or $C_{1-4}$ alkanoyl; or $R_3$ and $R_4$, together with each other, are —CO—;

$R_5$ is hydrogen, $C_{1-8}$ alkyl, lower alkenyl, phenyl or $C_{3-7}$ cycloalkyl;

$R_6$ is —$NR_7R_8$, morpholino, pyrrolidino, piperidino, —NH—$NH_2$, —NH—N=$CR_{11}R_{12}$ or

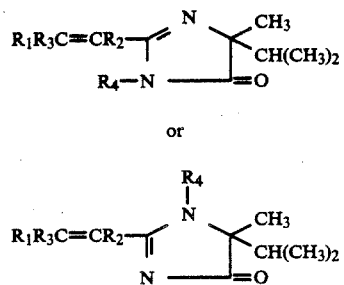

$R_7$ is hydrogen, lower alkyl, lower alkenyl, phenyl, or hydroxyl;

$R_8$ is hydrogen, lower alkyl, lower alkenyl or phenyl;

$R_9$ and $R_{10}$ are each independently lower alkyl;

$R_{11}$ is hydrogen or lower alkyl;

$R_{12}$ is lower alkyl; and

M is one equivalent of an alkali metal, ammonium or alkaline earth metal ion.

2. A compound of claim 1 of the formula

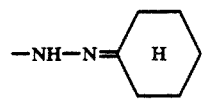

wherein $R_1$ and $R_2$ are each independently lower alkyl;

$R_3$ is —$COOR_5$, —$COR_6$ or —CN;

$R_4$ is hydrogen or $C_{1-4}$ alkanoyl; or $R_3$ and $R_4$, together with each other, are —CO—;

$R_5$ is hydrogen, lower alkyl, lower alkenyl or $C_{5-7}$ cycloalkyl;

$R_6$ is —$NR_7R_8$, morpholino, pyrrolidino or piperidino;

$R_7$ is hydrogen, lower alkyl, phenyl or hydroxyl; and $R_8$ is hydrogen, lower alkyl or phenyl.

3. A compound of claim 1 of the formula

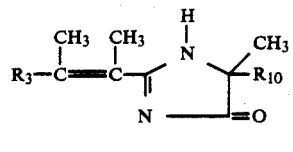

or

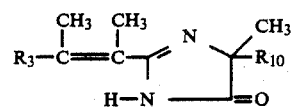

wherein $R_3$ is —$COOC_2H_5$, —COO—n—$C_3H_7$, —COO—i—$C_3H_7$,

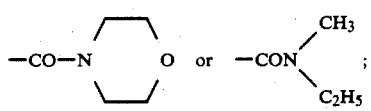

and $R_{10}$ is ethyl or isopropyl.

4. A compound of the formula

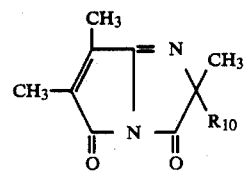

wherein $R_{10}$ is ethyl or isopropyl.

5. An herbicidal composition consisting essentially of an inert carrier and an effective herbicidal amount of a compound of claim 1.

6. An herbicidal composition consisting essentially of an inert carrier and an effective herbicidal amount of a compound of claim 4.

7. The method of killing dicotyledonous and monocotyledonous weeds, which comprises contacting said weeds with an effective herbicidal amount of a compound of claim 1.

8. The method of killing dicotyledonous and monocotyledonous weeds, which comprises contacting said weeds with an effective herbicidal amount of a compound of claim 4.

* * * * *

UNITED STATES PATENT AND TRADEMARK OFFICE
CERTIFICATE OF CORRECTION

PATENT NO. : 4,723,989
DATED : February 9, 1988
INVENTOR(S) : Wolfgang Buck et al.

It is certified that error appears in the above-identified patent and that said Letters Patent is hereby corrected as shown below:

Column 11, lines 7-10: That portion of the formula which now reads 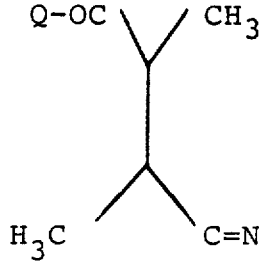

should read 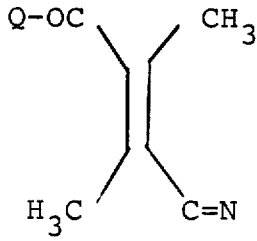

Signed and Sealed this

Sixteenth Day of August, 1988

Attest:

DONALD J. QUIGG

Attesting Officer

Commissioner of Patents and Trademarks

Notice of Adverse Decision in Interference

In Interference No. 102,174, involving Patent No. 4,723,989, W. Buck, M. Garrecht, G. Schneider, C. Drandarevski, HERBICIDAL IMIDAZOLINONES, final judgment adverse to the patentees was rendered Mar. 9, 1990, as to claims 1-8.

(*Official Gazette May 8, 1990*)